US00PP19403P2

(12) United States Plant Patent
Hop

(10) Patent No.: US PP19,403 P2
(45) Date of Patent: Nov. 4, 2008

(54) ***ASTER* PLANT NAMED 'STARSHINE'**

(50) Latin Name: *Aster ageratoides*
Varietal Denomination: Starshine

(76) Inventor: Margareth E. C. M. Hop, P.O. Box 85, 2160 AB, Lisse (NL)

( * ) Notice: Subject to any disclaimer, the term of this patent is extended or adjusted under 35 U.S.C. 154(b) by 0 days.

(21) Appl. No.: 11/974,218

(22) Filed: Oct. 11, 2007

(51) Int. Cl.
*A01H 5/00* (2006.01)

(52) U.S. Cl. ..... Plt./355
(58) Field of Classification Search ..... Plt./355
See application file for complete search history.

(56) References Cited

PUBLICATIONS

UPOV–ROM search for PBR 2006732 for cultivar Starshine. Page 1.*

* cited by examiner

*Primary Examiner*—Annette H Para
(74) *Attorney, Agent, or Firm*—C. A. Whealy

(57) ABSTRACT

A new and distinct cultivar of *Aster* plant named 'Starshine', characterized by its uniform, sturdy, upright, outwardly spreading and mounding plant habit; freely flowering habit; daisy-type inflorescences with white-colored ray florets; tolerance to Powdery Mildew; and good garden performance.

2 Drawing Sheets

Botanical designation: *Aster ageratoides.*
Cultivar denomination: 'Starshine'.

BACKGROUND OF THE INVENTION

The present invention relates to a new and distinct cultivar of *Aster* plant, botanically known as *Aster ageratoides* and hereinafter referred to by the name 'Starshine'.

The objective of the breeding program is to create new pot-type-type *Aster* cultivars with compact growth habit, attractive ray floret coloration and tolerance to Powdery Mildew.

The new *Aster* originated from an open-pollination in August, 1999 in Boskoop, The Netherlands of an unnamed seedling selection of *Aster ageratoides,* not patented, as the female, or seed, parent with an unknown selection of *Aster ageratoides,* not patented, as the male, or pollen, parent. The new *Aster* was discovered and selected by the Inventor as a single flowering plant within the progeny of the stated open-pollination in a controlled environment in Boskoop, The Netherlands in August, 2002.

Asexual reproduction of the new *Aster* by vegetative cuttings was first conducted in Boskoop, The Netherlands during the spring of 2003. Asexual reproduction by cuttings has shown that the unique features of this new *Aster* are stable and reproduced true to type in successive generations.

SUMMARY OF THE INVENTION

Plants of the cultivar Starshine have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Starshine'. These characteristics in combination distinguish 'Starshine' as a new and distinct pot-type *Aster* cultivar:

1. Uniform, sturdy, upright, outwardly spreading and mounding plant habit.

2. Freely flowering habit.
3. Daisy-type inflorescences with white-colored ray florets.
4. Tolerance to Powdery Mildew.
5. Good garden performance.

Plants of the new *Aster* differ from plants of the female parent selection primarily in ray floret color as plants of the female parent selection have pale purple-colored ray florets.

Plants of the new *Aster* can be compared to plants of the *Aster ageratoides* cultivar Ashvi, not patented. In side-by-side comparisons conducted in Boskoop, The Netherlands, plants of the new *Aster* differed from plants of the cultivar Ashvi in the following characteristics:

1. Plants of the new *Aster* were more compact than plants of the cultivar Ashvi.
2. Plants of the new *Aster* had sturdier stems than plants of the cultivar Ashvi.
3. Plants of the new *Aster* flowered earlier than plants of the cultivar Ashvi.

BRIEF DESCRIPTION OF THE PHOTOGRAPHS

The accompanying photographs illustrate the overall appearance of the new *Aster.* These photographs show the colors as true as it is reasonably possible to obtain in colored reproductions of this type. Colors in the photographs may differ slightly from the color values cited in the detailed botanical description which accurately describe the colors of the new *Aster.*

The photograph on the first sheet comprises a side perspective view of a typical flowering plant of 'Starshine' grown in a container.

The photograph at the top of the second sheet is a close-up view of typical inflorescences of 'Starshine'.

The photograph at the bottom of the second sheet is a close-up view of a typical leaf of 'Starshine'.

DETAILED BOTANICAL DESCRIPTION

The aforementioned photographs and following observations and measurements describe plants grown during September in an outdoor nursery in Boskoop, The Netherlands in five-liter containers and under conditions and practices which approximate those generally used in commercial container *Aster* production. During the production of the plants, day temperatures ranged from 12° C. to 26° C. and night temperatures ranged from 4° C. to 14° C. Plants used in the photographs and for the description were about three years old. In the following description, color references are made to The Royal Horticultural Society Colour Chart, 2001 Edition, except where general terms of ordinary dictionary significance are used.

Botanical classification: *Aster ageratoides* cultivar Starshine.

Parentage:

*Female, or seed, parent.*—Unnamed seedling selection of *Aster ageratoides,* not patented.

*Male, or pollen, parent.*—Unknown selection of *Aster ageratoides,* not patented.

Propagation:

*Type.*—Terminal vegetative cuttings.

*Time to initiate roots.*—About three weeks at temperatures of about 15° C. to 25° C.

*Time to produce a rooted young plant, summer.*—About three months at temperatures of about 15° C. to 25° C.

*Time to produce a rooted young plant, winter.*—About 3.5 months at temperatures of about 15° C. to 25° C.

*Root description.*—Moderately thick, fibrous; white in color.

*Rooting habit.*—Freely branching; dense.

Plant description:

*Appearance.*—Perennial daisy-type pot-type *Aster.* Uniform, sturdy, upright, outwardly spreading and mounding plant habit; broad inverted triangle with lateral branches somewhat outwardly spreading. Strong and freely branching growth habit with about 40 primary lateral branches. Moderately vigorous growth habit.

*Plant height.*—About 58 cm.

*Plant width.*—About 94 cm.

*Lateral branches.*—Length: About 40.1 cm. Diameter: About 3 mm. Internode length: About 1.4 cm. Strength: Strong. Texture: Pubescent. Color: 143A.

Foliage description:

*Arrangement.*—Alternate, simple; sessile.

*Length.*—About 5.2 cm.

*Width.*—About 2.1 cm.

*Shape.*—Elliptic to oblong.

*Apex.*—Acute.

*Base.*—Attenuate.

*Margin.*—Serrate.

*Texture, upper and lower surfaces.*—Pubescent; rough.

*Color.*—Developing foliage, upper surface: 137A. Developing foliage, lower surface: 138A. Fully expanded foliage, upper surface: Between 137A and 139A; venation, 137B. Fully expanded foliage, lower surface: 137B; venation, 137C.

Inflorescence description:

*Appearance.*—Daisy-type inflorescence form with narrowly oblong to obovate-shaped ray florets. Inflorescences face mostly upright and are borne on terminals above and beyond the foliage. Disk and ray florets arranged acropetally on a capitulum. Inflorescence faintly fragrant, slightly musty.

*Flowering response.*—Under natural conditions, plants flower continuously from mid-August to early October in The Netherlands. Inflorescences not persistent. Inflorescences last about three weeks on the plant.

*Quantity of inflorescences.*—Freely flowering, about 3,600 inflorescences develop per plant over the flowering period.

*Inflorescence bud.*—Height: About 6 mm. Diameter: About 4 mm. Shape: Obovate. Color: 145A to 145B.

*Inflorescence size.*—Diameter: About 2.9 cm. Depth (height): About 1 cm. Diameter of disc: About 1.1 cm. Receptacle height: About 6 mm. Receptacle diameter: About 5 mm.

*Ray florets.*—Length: About 1.6 cm. Width: About 2.2 mm. Shape: Narrowly oblong to obovate. Apex: Praemorse. Base: Cuneate. Margin: Entire. Texture, upper and lower surfaces: Smooth, glabrous, satiny. Orientation: Initially upright, then about 90° from vertical or perpendicular to peduncle, eventually apices reflexed. Number of ray florets per inflorescence: About 25 arranged in about two whorls. Color: When opening, upper and lower surfaces: Close to 155A. Fully opened, upper and lower surfaces: Close to 155D.

*Disc florets.*—Arrangement: Massed at center of receptacle. Shape: Tubular, elongated. Apex: Five-pointed. Length: About 8 mm. Width, apex: About 2 mm. Width, base: Less than 1 mm. Number of disc florets per inflorescence: About 50. Color: Immature: 153C to 153D. Mature: Apex: 9B to 9C. Mid-section: 1B to 1C. Base: 150D.

*Phyllaries.*—Number of phyllaries per inflorescence: About 30 arranged in about three whorls. Length: About 4 mm. Width: About 1 mm. Shape: Narrowly oblong. Apex: Broadly acute. Base: Cuneate. Texture, upper surface: Smooth, glabrous; at the margins, pubescent. Texture, lower surface: Pubescent. Color, upper and lower surfaces: N144D; towards the apex, between 144B and N144A; towards the margins, 145C to 145D.

*Peduncles.*—Length, terminal peduncle: About 2.6 cm. Length, fourth peduncle: About 9.5 cm. Diameter: About 2 mm. Angle: Upright to about 35° from vertical. Strength: Strong. Texture: Smooth, glabrous. Color: 143A.

*Reproductive organs.*—Androecium: Present on disc florets only. Anther shape: Lanceolate. Anther length: About 2 mm. Anther color: 9B. Pollen amount: Moderate. Pollen color: 9A to 9B. Gynoecium: Present on both ray and disc florets. Pistil length: About 4 mm. Stigma shape: Bi-parted. Stigma color: 5C. Style length: About 3 mm. Style color: Close to 150D. Ovary color: Close to 145D.

*Seeds.*—Length: About 7 mm. Diameter: Less than 1 mm. Color: N200A.

Disease/pest resistance: Plants of the new *Aster* have been observed to be tolerant to Powdery Mildew. Resistance to pests and other pathogens common to *Asters* has not been observed on plants grown under commercial conditions.

Garden performance: Plants of the new *Aster* have been observed to tolerate rain, wind and temperatures ranging from about −15° C. to about 35° C.

It is claimed:

1. A new and distinct *Aster* plant named 'Starshine' as illustrated and described.

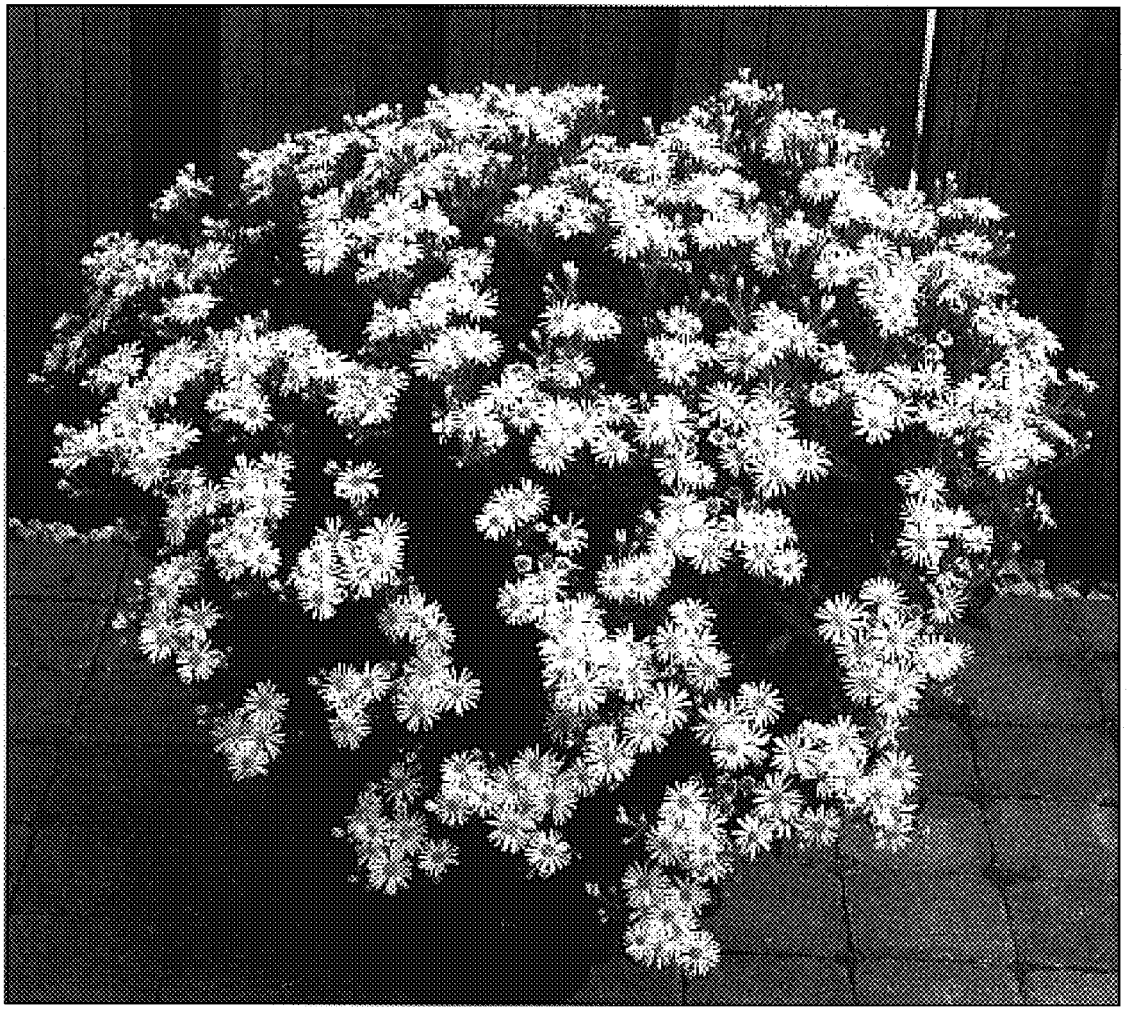

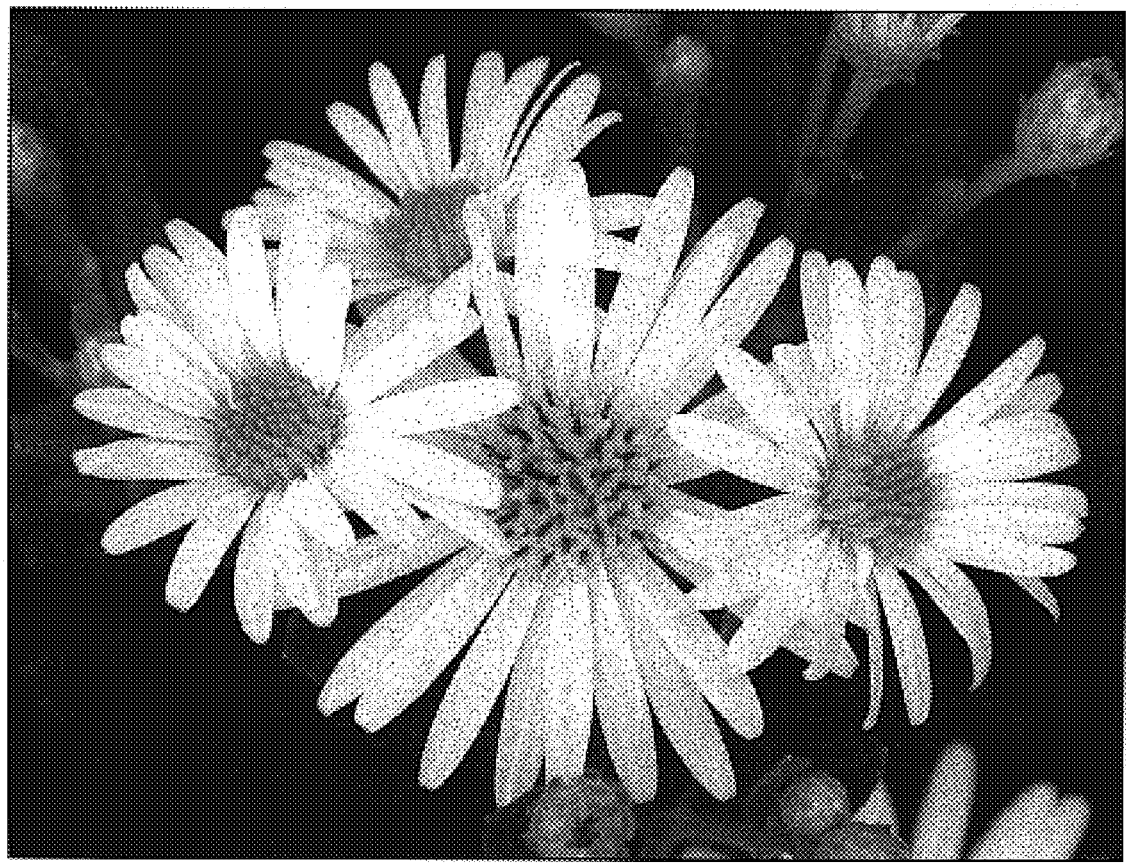
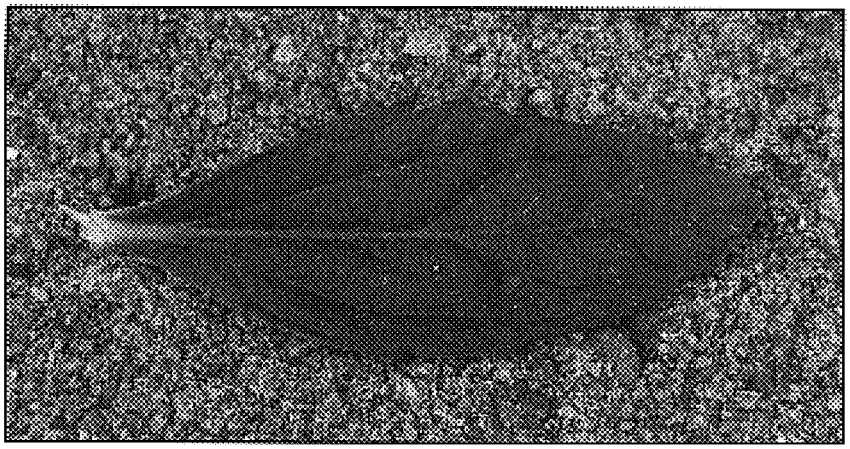

* * * * *